United States Patent
Nicholson et al.

(10) Patent No.: US 6,524,316 B1
(45) Date of Patent: *Feb. 25, 2003

(54) BONE FASTENER

(75) Inventors: James E. Nicholson, Lincoln, MA (US); Rickey D. Hart, North Attleboro, MA (US); John Rice, Lincoln, MA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/332,965

(22) Filed: Jun. 14, 1999

Related U.S. Application Data

(60) Division of application No. 08/814,149, filed on Mar. 10, 1997, now Pat. No. 5,911,721, which is a continuation of application No. 08/163,130, filed on Dec. 6, 1993, now Pat. No. 5,725,529, which is a continuation-in-part of application No. 07/765,445, filed on Sep. 25, 1991, now Pat. No. 5,268,001, which is a continuation-in-part of application No. 07/588,055, filed on Sep. 25, 1990, now abandoned.

(51) Int. Cl.$^7$ ............................................. A61B 17/58
(52) U.S. Cl. ............................ 606/72; 606/75; 411/45
(58) Field of Search ............................ 606/61, 69, 72, 606/73, 75, 70, 71, 232; 411/531, 533, 534, 41, 45–48, 72

(56) References Cited

U.S. PATENT DOCUMENTS

| | | | |
|---|---|---|---|
| 3,760,802 A | * 9/1973 | Fischer et al. | 411/50 |
| 4,475,856 A | * 10/1984 | Toomingas | 411/47 |
| 4,797,044 A | * 1/1989 | Velasco | 411/51 |
| 4,988,351 A | * 1/1991 | Paulos et al. | 606/72 |
| 5,314,427 A | * 5/1994 | Goble et al. | 606/72 |
| 5,352,229 A | * 10/1994 | Goble et al. | 606/72 |
| 5,725,529 A | * 3/1998 | Nicholson et al. | 606/72 |
| 5,800,436 A | * 9/1998 | Lerch | 606/72 |

* cited by examiner

Primary Examiner—Julian W. Woo
(74) Attorney, Agent, or Firm—Nutter, McClennen & Fish LLP

(57) ABSTRACT

A bone fastener including an expandable member having an axial channel and an elongated element insertable into the axial channel is described. The expandable member is configured to be insertible into a bore drilled in bone. The distal end of the expandable member also may include a structure for axially releasing the expandable member from an emplacement device that places the expandable member into a bone opening. In one embodiment, the structure for axially releasing includes a frangible membrane capable of being severed from the expandable member during emplacement of the expandable member in a bone opening.

A rivet for coupling an object to bone for use with an expandable member is also described. The distal end of the elongated element is shaped into a radially projecting portion adapted for engagement with a washer that contacts the object to be coupled. The washer, having upper and lower surfaces and a bore defined between the surfaces, is disposed around a portion of the shaft. The elongated element is adapted for movement independent of the washer since the radial projection of the element has a different radius of curvature than the washer.

An apparatus for use within an endoscope is described. The apparatus includes an elongated, substantially hollow holding means for emplacing a bone fastener of the invention in a bone opening. The expandable member includes a structure for axially releasing the expandable member from the holding means. A method of attaching soft tissue to bone is also described. The invention also includes a surgical fastener kit.

4 Claims, 12 Drawing Sheets

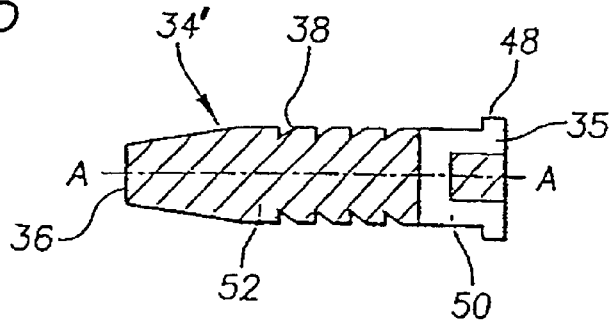
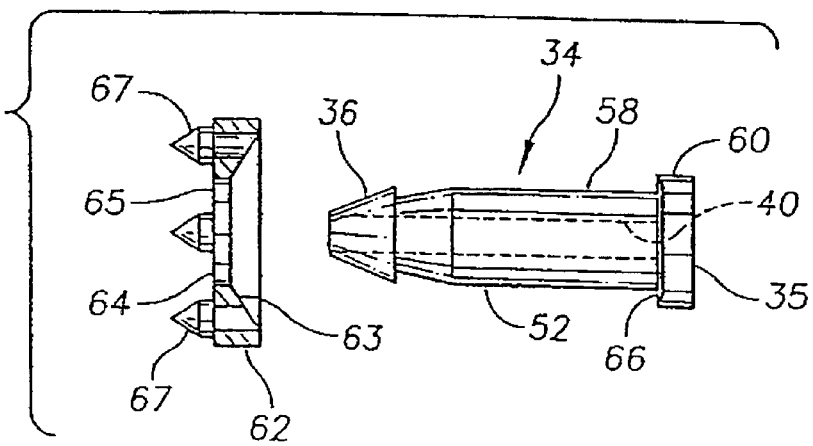
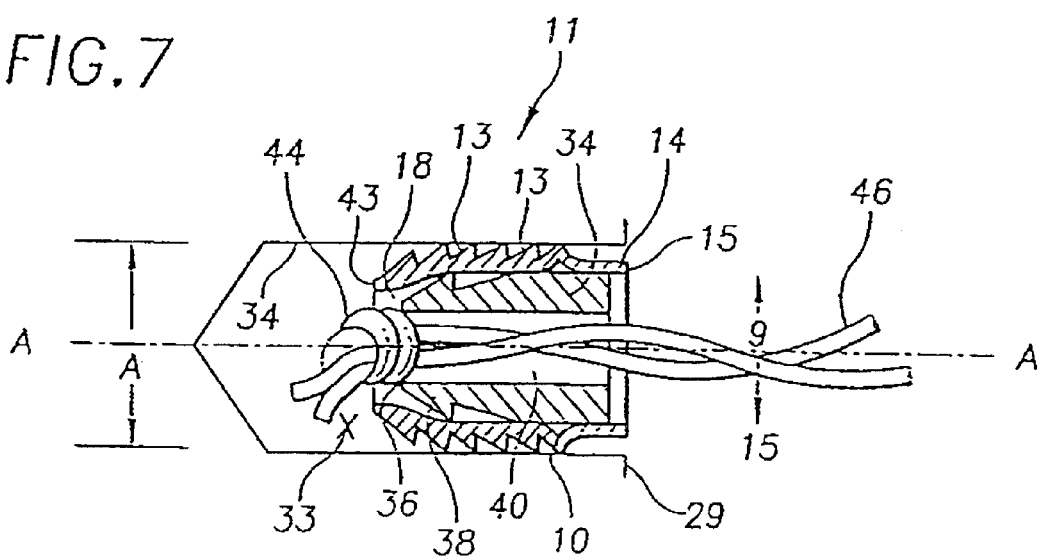

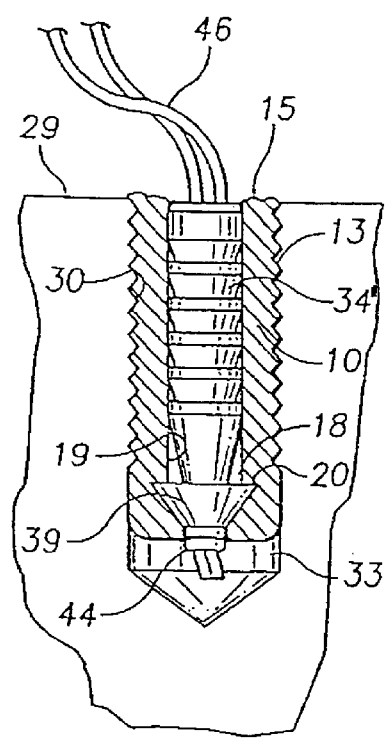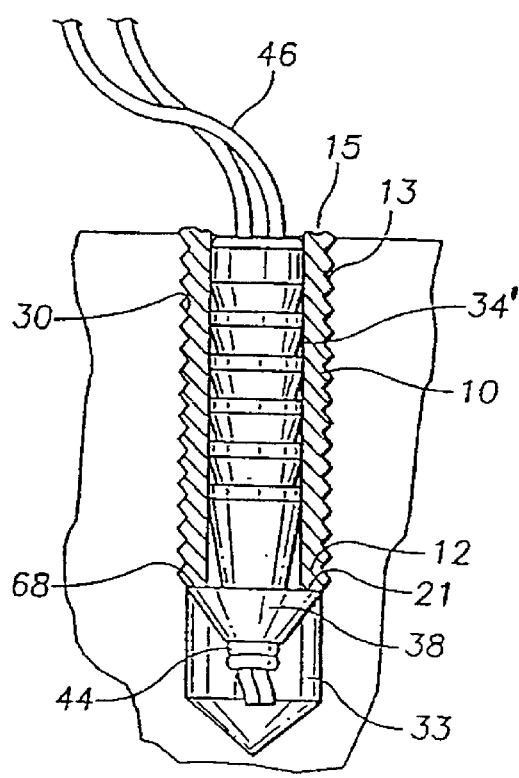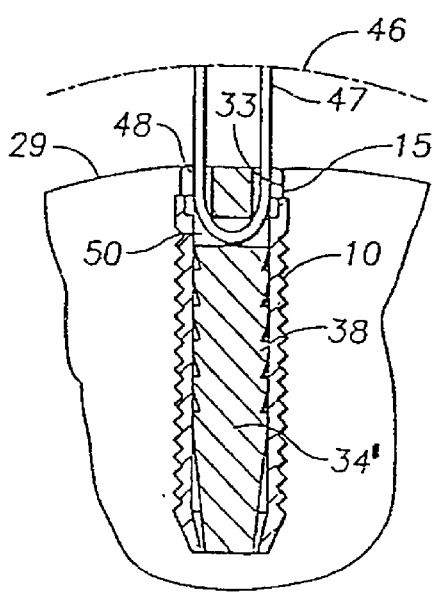

FIG. 13
FIG. 14
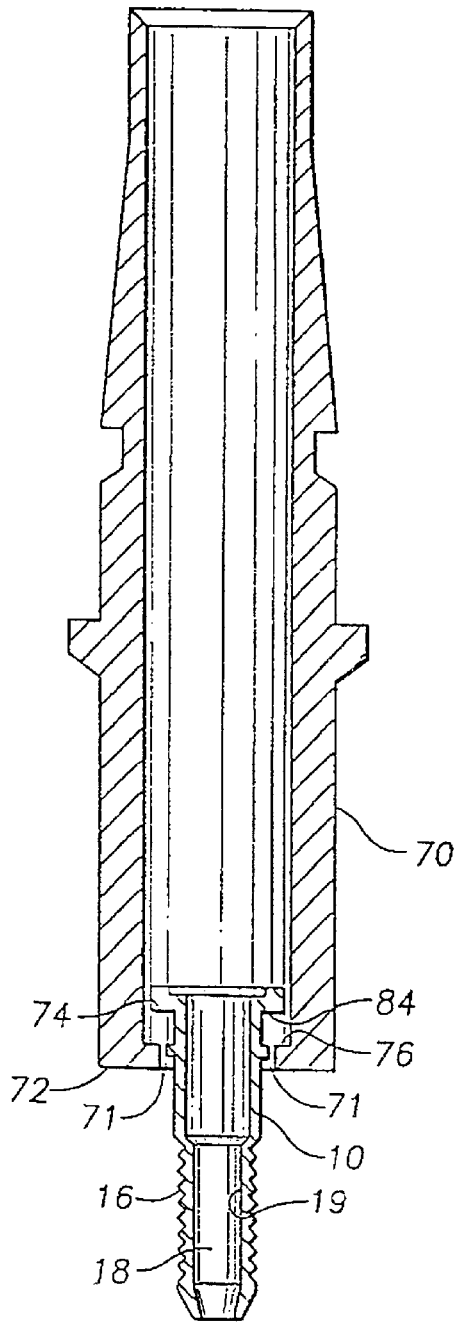
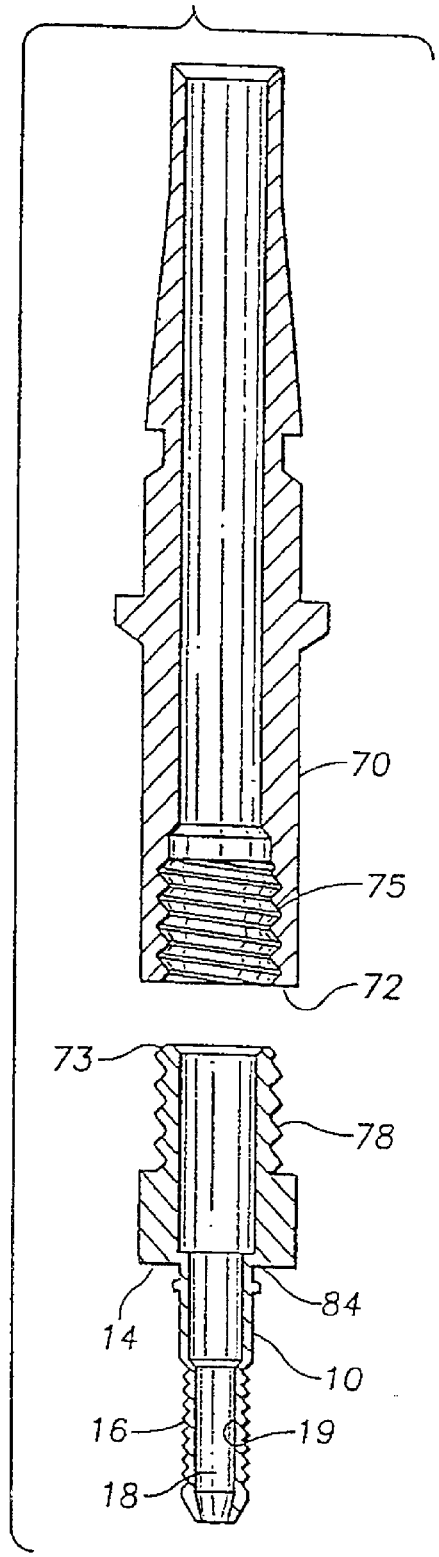

BONE FASTENER

This application is a divisional of U.S. Ser. No. 08/814,149, filed Mar. 10, 1997, which will issue as U.S. Pat. No. 5,911,721 on Jun. 15, 1999, which is a continuation of U.S. Ser. No. 08/163,130, filed Dec. 6, 1993, now U.S. Pat. No. 5,725,529, which is a continuation-in-part of U.S. Ser. No. 07/765,445, filed Sep. 25, 1991, now U.S. Pat. No. 5,268,001, which is a continuation-in-part of U.S. Ser. No. 07/588,055, filed Sep. 25, 1990, now abandoned; the entire contents of these applications are incorporated herein by reference.

BACKGROUND OF THE INVENTION

A variety of techniques are available for affixing objects such as soft tissue to bone. The oldest technique utilizes thread passed through the bone and the tissue to sew the tissue down to the bone. Many sizes, shapes and types of suture and suture needles are available to accomplish this task. Today, this method is still used for repair of tendons and ligaments in older osteoarthritic patients, although passing a suture through bone is generally difficult and tedious.

Soft tissue repairs also have been accomplished with metal screws or staples that attach soft tissue to bone. Metal screws and/or staples are, however, subject to corrosion and consequent loss of structure. Moreover, the presence of metal in an anatomical site can interfere with imaging and diagnostic or therapeutic treatments near the site. For example, any metal implants may have to be removed by surgery prior to magnetic resonance imaging. Patient sensitivity to nickel ions and stainless steel implants has fueled a growing controversy regarding the use of materials containing high quantities of nickel including nickel-titanium alloys such as Nitinol. Also, it is almost impossible to adjust the compression exerted by screws and staples on soft tissue. Thus, these devices are not fully satisfactory for soft tissue repair.

Other devices employ a suture anchor installation affixed to an arc of wire or a plurality of barbs disposed on an outer surface of the suture anchor body. The barbs or arc of wire are set by applying traction to the suture. Unfortunately, it is not always possible to position the anchor at a precise location within a bone if an anchor is being drawn upwards in a bone hole by applying tension to a suture. Furthermore, many of the fastening devices require some type of impact or impulse to set the fastener in position. Impact emplacement or setting of bone/suture anchors may result in injury to the patient as well as placing unnecessary strain on the bone/suture fastener itself.

SUMMARY OF THE INVENTION

The present invention is directed to a novel apparatus for emplacing a bone fastener that eliminates the problems created by conventional bone fastener emplacement devices.

In general, the invention features a bone fastener including an expandable member having an axial channel and an elongated element inserted into the axial channel. The expandable member is configured to be insertible into a bore drilled in bone. The member is expanded using a continuous, compressive force (i.e., pressure without impulse or impact). The expandable member is grasped at its distal end throughout the emplacement procedure and is axially released from an emplacement tool.

In one embodiment, a fastener for coupling an object to a bone is described. The fastener includes a cylindrical expandable member for insertion into an opening in a bone, the member including an outer surface for expandable engagement with an inner surface of the bone opening. An axial channel is defined in the expandable member, the channel extending at least partially between proximal and distal ends of said expandable member. An elongated, insertion element that is compressed into the expandable member is also part of the fastener. The insertion element has proximal and distal ends and a channel defined between the ends for engagement with a suture. Preferably, the insertion element includes a projection that expands the axial channel of the expandable member in an irreversible manner to obtain a press-fit with the bone opening. In preferred embodiments, the outer surface of the expandable member includes a plurality of projections for engagement with the inner surface of the bone opening. The distal end of the expandable member also may include a structure for axially releasing the expandable member from an emplacement device that places the expandable member into a bone opening. In one embodiment, the structure for axially releasing includes a frangible membrane capable of being severed from the expandable member during emplacement of the expandable member in a bone opening.

The invention also pertains to a rivet for coupling an object to bone for use with an expandable member capable of insertion into an opening in a bone. The rivet includes an elongated insertion element adapted for compression into a distal end of the expandable member. The insertion element has a shaft with proximal and distal ends, an outer surface of said shaft including a radially outward projecting portion adapted to expand the expandable member. The distal end of the elongated insertion element includes a radially projecting portion adapted for engagement with a washer that contacts the object to be coupled. The washer, having upper and lower surfaces and a bore defined between the surfaces, is disposed around the shaft of the insertin element. The element is adapted for movement independent of the washer since the radial projection of the insertion element has a different radius of curvature than the washer.

The invention further includes the combination of a bone; an opening defined in the bone and an expandable member inserted into the opening in the bone. The expandable member includes an elongated, insertible element, as described above, and further includes at its distal end, at least part of a means for axially releasing the expandable member from a holder, the holder for emplacing the expandable member in the bone opening.

In preferred embodiments, the expandable member and insertible element are formed out of a bioabsorbable polymer such as polylactide, polyglycolide and combinations thereof.

The invention also pertains to an apparatus for use within an endoscope. The apparatus includes an elongated, substantially hollow holding means for emplacing a bone fastener in a bone opening, the holding means having distal and proximal ends. An expandable member having a proximal end and a distal end integral with the proximal end of the holding means is also included. In one embodiment, the expandable member includes a structure for axially releasing the expandable member from the holding means. The structure may be a frangible membrane disposed intermediate the proximal end of the holding means and the distal end of the expandable member.

A method of attaching soft tissue to bone is also described. The method includes providing an expandable member for insertion into an opening in a bone. The member has defined in it an axial channel having a certain diameter. The member also includes a structure for axially releasing the expandable member from a holding means. Next, the expandable member is engaged at a distal end thereof by way of the emplacement means. The expandable member is inserted into soft tissue and bone while maintaining engagement with the distal end of the expandable member. A continuous, compressive force is then applied to the expandable member to expand the diameter of the axial channel so that an outer surface of the expandable member engages with the bone. The structure for axially releasing the expandable member is then activated, so that the expandable member is released from the emplacement means when the continuous force stops.

An apparatus for placing a bone fastener in an opening in a bone includes the combination of an expandable member with an axial channel defined therein; an elongated, substantially hollow holder for the expandable member, an insertion element for engagement with an inner surface of the axial channel; a structure for axially releasing the expandable member from the holder when the expandable element is fully expanded within the bone opening; a structure adapted for co-axial movement relative to the holder for placing the element into the axial channel of the expandable member; and a structure co-axially moveable within the hollow body for releasing the expandable member from the holder.

The invention also includes a surgical fastener kit. The kit includes an expandable member for insertion into an opening of the bone, the member having an axial channel defined in it and an outer surface for engaging an inner surface of the bone opening. The kit also includes an element for insertion into the axial channel. This element has a projecting surface for engaging the inner surface of the axial channel. This kit also includes a holder for engaging with the expandable member, the holder capable of maintaining the expandable member in position with the bone opening. In other embodiments of the kit, a grasper/manipulator for the suture, a drill and a retrieval device are also included. Preferably, the kit is encased in a sterile tray or other receptacle for use by an operator at a site.

It is an object of the present invention to provide a bone fastener of simple design and construction.

It is another object of the present invention to provide a bone fastener having one or more bioabsorbable components.

It is a further object of the present invention to provide a bone fastener that can be set within a bone hole without requiring the need for a suture.

It is yet another object of the present invention to provide an apparatus for emplacing a bone fastener that does not require an impact or impulse in order to deploy the fastener and that allows the operator to adjust the force attaching a tissue to a bone.

It is another object of the present invention to provide a method for emplacing the bone fastener that eliminate the use of nitinol barbs or other similar devices.

It is yet another object of the present invention to provide an apparatus for inserting a bone fastener that can be used arthroscopically.

BRIEF DESCRIPTION OF THE DRAWINGS

FIG. 5 is a cross-section of another embodiment of an insertion element of the invention;

FIG. 6 is a perspective view of another embodiment of an insertion element and washer of the present invention;

FIG. 7 illustrates in a less diagrammatic cross-sectional view, a suture fastener of the invention emplaced in a pre-drilled hole in bone. This Figure shows deformation of the outer portion of expandable member within irregularities in the bone hole wall;

FIG. 8 is a cross-section of an embodiment of the bone fastener in which a proximal projection extends out of the proximal end of the expandable member;

FIG. 9 is a cross-section of a further embodiment of FIG. 8;

FIG. 10 is a cross-section of an elongated, slidable suture insertion element of FIG. 5 in place within expandable element in a bone opening;

FIG. 13 is a cross-section of one embodiment of expandable member and holding means of the invention;

FIG. 14 is a cross-section of another embodiment of an expandable member and holding means of the invention;

DETAILED DESCRIPTION OF THE INVENTION

The bone fastener, according to the invention, generally includes an elongated insertion element and an approximately cylindrical expandable member with an axial channel for receiving the insertion element. In its unexpended state, the expandable member can be placed into a pre-drilled opening in a bone. A diameter of at least a portion of the insertion element is greater than that of at least a portion of the axial channel so that, when the element is inserted into the axial channel, the wider portion of the insertion element is forced outward against the axial channel. The axial channel is susceptible to enlargement by this force acting substantially orthogonal to the axial channel. This outward force causes the expandable member to expand ineversibly against the wall of the opening, fixing the insertion element within the expandable member and fixing the expandable member in a pressure fit firmly within the opening. As described in more detail below, the insertion element or the expandable member, or both of them, can be adapted to provide a fastener for attaching soft tissue using a suture or to provide a rivet for attachment without a suture.

A. The Expandable Member

Figure 1:
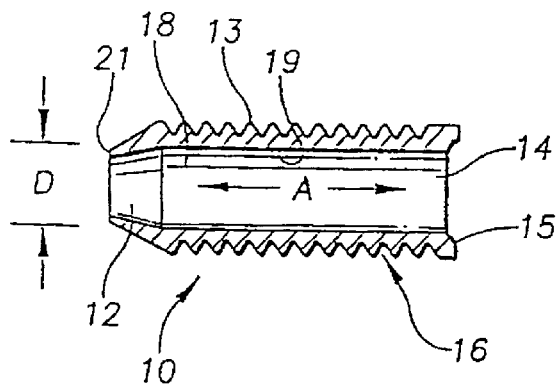
FIG. 1 is a cross-section through the expandable member of the present invention.

An embodiment of the expandable member 10 of the present invention is illustrated in FIG. 1. The expandable member is a substantially cylindrical body having one and another ends; a proximal end 12 that first enters the bone opening and a distal end 14 farthest away from the proximal end. The expandable member is preferably constructed of a biocompatible material that is sufficiently deformable so that, when expanded within a bone opening, the member will conform to a substantial degree with the irregularities in the bone opening wall. The term "biocompatible" means that the expandable member material is chemically and biologically inert. Suitable materials for the expandable member include, for example, an implant grade high density polyethylene, low density polyethylene (PE 6010 and PE 2030) and polypropylene (13R9A and 23M2: all made by Rexene, Dallas, Tex.). Of these, PE 6010 and 13R9A have been FDA listed as class 6 materials.

The expandable member may also be bioabsorbable. The term "bioabsorbable" refers to those materials that are meant to be decomposed or degraded by bodily fluids, such as, for example, blood and lymph. The expandable member is preferably made from a biodegradable polymer or copolymer of a type selected in accordance with the desired degradation time. That time in turn depends upon the anticipated healing time of the tissue which is the subject of the surgical procedure. Known bioabsorbable polymers and copolymers range in degradation time from about 3 months for polyglycolide to about 48 months for polyglutamic-co-leucine. A common bioabsorbable polymer used in absorbable sutures is poly (L-lactide) which has a degradation time of about 12 to 18 months. The preferred expandable member is comprised of an absorbable copolymer derived from glycolic and lactic acids, such as a synthetic polyester chemically similar to other commercially available glycolide and lactide copolymers. Glycolide and lactide degrade and absorb in the body by hydrolysis into lactic acid and glycolic acid which are then metabolized by the body.

The following Table set forth below lists polymers which are useful for the bioabsorbable material employed for the expandable member, and other parts of the bone fastener as described below. These polymers are all biodegradable into water-soluble, non-toxic materials which can be eliminated by the body. Their safety has been demonstrated and they are listed as approved materials by the U.S. Food and Drug Administration.

TABLE

Polycaprolactone
Poly(L-lactide)
Poly(DL-lactide)
Polyglycolide
95:5 Poly(DL-lactide-co-glycolide)
90:10 Poly(DL-lactide-co-glycolide)
85:15 Poly(DL-lactide-co-glycolide)
75:25 Poly(DL-lactide-co-glycolide)
50:50 Poly(DL-lactide-co-glycolide)
90:10 Poly(DL-lactide-co-caprolactone)
75:25 Poly(DL-lactide-co-caprolactone)
50:50 Poly(DL-lactide-co-caprolactone)
Polydioxanone
Polyesteramides
Copolyoxalates
Polycarbonates
Poly(glutamic-co-leucine)

Referring to FIG. 1, the expandable member 10 includes an outer surface 13 for secured engagement with an inner surface of a bone opening. Outer surface 13 can be smooth or can be provided with a plurality of ridges 16 as shown. In particular, a preferred configuration includes a plurality of annular ridges for engaging irregularities in the bone opening wall as the expandable member 10 deforms and conforms to the bone opening wall during and after expansion. It will be appreciated that ridges 16 may also be axially aligned with the long axis (shown by arrow A in FIG. 1) of the expandable member. The shape and design of the outer surface ridges 16 are not intended to limit the scope of the invention in any way.

The ability of the expandable member to conform to the inner dimensions of a bone opening may be augmented considerably by providing the outer surface of the expandable member with one or more slots (not shown) extending between the proximal and distal ends of the expandable member, the ends of the slots disposed at some distance remote from the proximal and distal ends of the expandable member. That is, the ends of the slots are not in contact with the ends of the expandable member. The slots allow the member to flex and conform to irregularities in the bone hole. The slots may be run axially or circumferentially along the outer surface of the expandable member.

An axial channel 18 is defined between the ends 12, 14 of the expandable member 10 and preferably extends completely through the expandable member. The axial channel 18 has a certain inner diameter, indicated by reference letter D in FIG. 1. The diameter may be substantially constant along the longitudinal axis (A) of the axial channel 18, although the diameter may also vary along one or more portions of the length of the channel. In one embodiment, (illustrated below in FIG. 9 ) one or more steps 20 are defined in the inner surface 19 of the axial channel 18. These steps are designed to mate with corresponding ridges on the outer surface of an insertion element (see below).

Referring again to FIG. 1, one end of the expandable member, (i.e. the proximal end 12) is specially adapted for insertion into the bone opening. This end is always of a diameter smaller than the inside diameter of the bone opening. The proximal end 12 of the expandable member 10 may include a substantially flat portion 21 for engagement with an outer surface of an insertion element (see FIG. 8).

Figure 2:
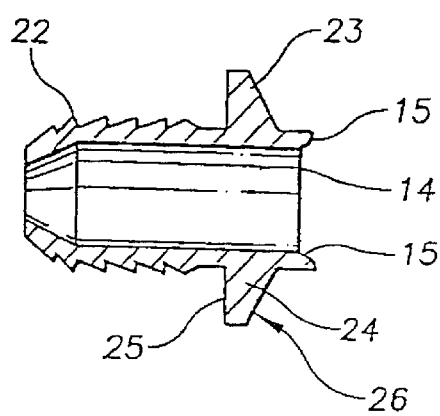
FIG. 2 is a cross-section through an expandable member of the present invention in which the distal end is configured to form a radial projection.

The expandable member 10 may also be adapted to form a rivet for directly affixing soft tissue, or an object such as a bone plate, to the bone at the fixation site. FIG. 2 shows an example of such a rivet 22, in which the distal end 14 of the expandable member is configured to form a radial projection 23. In FIG. 2, the projection is formed as a flange 24. The proximal surface 25 of flange 24 is generally planar and perpendicular to the longitudinal axis (A) of the member 10. The distal surface 26 of flange 24 is contoured to provide a smooth, generally dome shaped head, thinner near the margin than toward the center.

Figure 3:
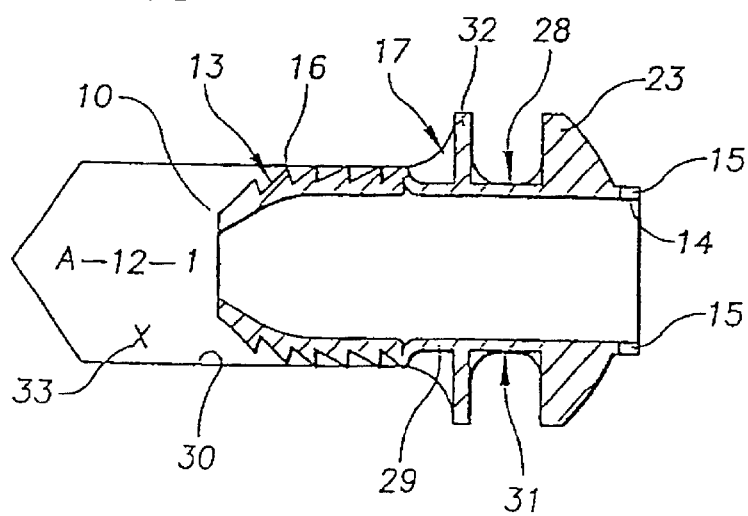
FIG. 3 is a cross-section through a rivet-type expandable member placed in a bone opening.

FIG. 3 illustrates a rivet-type expandable member 10 placed in a bone opening. The member 10 has a distal end 14 configured to form a radial projection 23 and a stand-off 28. The stand-off 28 is disposed between the radial projection 23 and a bone surface 29. The member 10 may have on its outer surface 13 a series of ridges 16 over an area that is to contact a bone opening wall 30 and a smooth section 31 over an area between the ridges 16 and the radial projection 23. The outer surface 13 of the expandable member 10 may also be provided with a stop 32 extending substantially orthogonal to the outer surface 13 of the member. Stop 32 is provided at the junction between the stand-off 28 and that portion of the outer surface 13 that contacts the bone wall 30 to limit precisely the depth to which the expandable member is inserted into the bone opening 33. In the embodiment illustrated, this stop 32 is formed as a pair of substantially rectangular protrusions, extending far enough out from the outer surface 13 of the member so that the protrusions contact the bone surface 29 at an edge 17 of the bone opening 33, stopping the frontward progress of the expandable member 10. When the operator senses the contact of the stop with the bone surface, a mechanism for inserting an insertion element can be activated, thus effecting fixation of the expendable member at the predetermined depth. Stand-off fasteners can be dimensioned to provide for various insertion depth and stand-offs, according to the particular surgical setting.

FIGS. 1–3 also illustrate a feature of the invention common to many embodiments of the expandable member; namely a structure 15 for axially releasing the expandable member from a holder device (not shown). The structure, described in more detail below, is preferably a membrane that is broken during emplacement of the bone fastener in a bone opening. The membrane is broken by a substantially continuous, non-impact force in a direction parallel to (i.e., axial to) the longitudinal axis of the expandable member. Structure 15 is disposed at a distal end of the expandable member 10 and is represented in FIG. 3 as a jagged, distal edge of projection 23. This is, when fully emplaced in a bone opening 33, the expandable member may retain a portion of the previously intact, axially releasing structure 15.

In other embodiments, not illustrated here, the outer surface of the expandable member can include self-tapping screw threads for engagement with the inner surface of the bone opening. The screw threads provide for positioning of the expandable member in the hole at its desired depth or for applying a desired force upon the object between a radial projection of the expandable member and the bone surface, prior to fixation by forcing the insertion element into the axial channel of the expandable member. In such a turnable screw thread configuration, the unexpended member can be turned into a bone hole having a diameter somewhat smaller than the outside diameter of the screw threads, so that the screw threads self-tap the hole to some extent as the member is turned into the hole. Although the threads are not meant to tap the bone hole to an extent sufficient by themselves to effect fixation of the member, surfaces of the screw threads can be hardened sufficiently to cut or abrade the bone hole wall. Such hardening can be provided, for example, by forming the member of a relatively deformable polymer material that can be hardened by application of heat or radiation, and then irradiating selective parts of the member outer surface to harden it at those parts. Ultimately, the softer material of the member can be provided over selective parts of its surface with a thin coating of a harder more durable material. Once such a self-tapping member has been turned into the bone hole to the desired depth, an insertion element can be forced into the axial channel of the member, expanding it and deforming the outer surface thereof as described above.

The expandable member may be fabricated by conventional molding or extrusion procedures and the sizes can vary over a wide range depending upon the particular surgical procedure. An exemplary expandable member can be about 0.40 inches (10.1 mm) long, with an outside diameter of about 0.140 inches (3.5 mm), the proximal opening of the axial channel being tapered to about 0.07 inches (1.7 mm).

B. The Insertion Element

Figure 4:
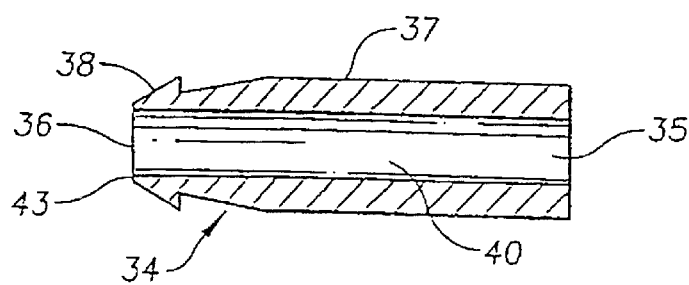
FIG. 4 is a cross-section of an insertion element the present invention.

FIG. 4 illustrates in diagrammatic cross-section an insertion element 34 of the present invention. The insertion element 34 is a substantially elongated shape having distal 35 and proximal 36 ends, and an outer surface 37. The outer surface, most preferably at one end, has a projection 38 for engagement with inner surface 19 of the axial channel 18 of expandable member 10 (see FIG. 1). Insertion element 34 may be constructed of a relatively hard biocompatible material such that the projection 38 expands the expandable member outwardly in a direction substantially orthogonal to the longitudinal axis of the expandable member. It will be appreciated that the projection 38 on the outer surface 37 of insertion element 34 can include a variety of configurations and designs. These configurations are not intended to limit the scope of the invention in any way.

A channel 40 is defined between ends 35,36 of the insertion element. The channel is adapted to engage a suture. In the embodiment illustrated, channel 40 extends completely between the opposed ends 35, 36 of insertion element 34. The insertion element at one of its ends, preferably the proximal end 36, includes a structure for attaching a suture. As illustrated in FIG. 7 below, the structure is most preferably an outer, flattened, peripheral wall 43 of insertion element 34. This outer wall is of sufficient width to engage a knot 44. Other means for attaching a suture may include, for example, one or more slots disposed at an end of the insertion element for trapping the knotted free ends of the suture within the jaws of the slot(s). Further, a suture attaching means can include a variety of clips or other devices.

The embodiment of FIG. 5 shows insertion element 34' provided with a channel to receive an intermediate portion of a suture (i.e., a segment between the free ends) to form a so-called "slidable" suture element. Insertion element 34' has a generally cylindrical shaft 52 provided with an expanded distal portion 48. A channel 50 is defined through the shaft 52 in a direction substantially at right angles to the longitudinal axis (A) of the shaft and may be located anywhere along the shaft. Preferably, the channel 50 is defined at, or adjacent to, the distal end 35 of the shaft 52. One or more projections 38 are provided for engaging the inner surface 19 of the expandable member's axial channel 18 (see FIG. 1). An intermediate portion of a suture thread may be engaged with channel 50. The expanded portion 48 at the distal end 35 of shaft 52 may be provided with a plurality of grooves, not shown. These grooves have a diameter sufficient to receive the suture thread, thus allowing the suture thread to lie flat and substantially parallel to the longitudinal axis of the insertion element without protruding.

FIG. 10 illustrates the elongated, slidable suture insertion element of FIG. 5 in place within expandable element 10 in bone opening 33. All reference numbers are identical to those shown previously. This particular fastener is designed to engage an intermediate portion 47 of suture 46.

Another embodiment of an insertion element of the present invention is provided in FIG. 6 which shows an insertion element 34 in the shape of a rivet 58. This rivet is for coupling an object to bone for use with the expandable member of the invention. Rivet 58 is an elongated element for insertion into the axial channel 18 of expandable member 10 (see FIG. 1), the rivet having a shaft 52 with distal and proximal ends 35, 36, respectively. Rivet 58 may have a channel 40 defined between the ends. A radial projecting portion 60 is provided at the distal end 35.

A washer 62 having an annular bore 64 may additionally be provided to enclose a portion of the shaft 52. The washer has upper 63 and lower 65 surfaces and bore 64 is defined between these surfaces as a single opening. The shaft 52 of the rivet is inserted within the bore.

The upper surface 63 of washer 62 is in facing relationship, and may be engaged with a lower surface 66 of the radial projection 60. Preferably, as shown in FIG. 6, the lower surface 65 of the washer includes a series of spaced-apart projections 67 extending away from the radial projection 60 and toward the proximal end 36 of the rivet. Spaced-apart projections 67, which may be of variable length, are intended to be inserted directly into the bone or into tissue distal to the bone and provide a grasping surface for the washer. The height of spaced-apart projections 67 provides sufficient distance between the washer and tissue so that the tissue will not undergo necrosis by being compressed too tightly by the washer or projection 60.

Most preferably, the outer diameter of the radial projection 60 is greater than the diameter of annular bore 64 of washer 62 which diameter, in turn, is greater than the outer diameter of rivet shaft 52. Thus, the bore of the washer is sufficiently large so that the washer can slide underneath the projection 60 of the rivet 58. This also provides sufficient distance between tissue and rivet to eliminate or substantially suppress tissue necrosis (see also FIG. 11). Moreover, the upper surface 63 of washer 62 and the lower surface 66 of radial projection 60 have a different radii of curvature. This differential radii of curvature allows the rivet to "float" between the tissue and the washer. It therefore allows the rivet to move relative to the washer to account for different orientations and angles of the bone surface.

Figure 11:
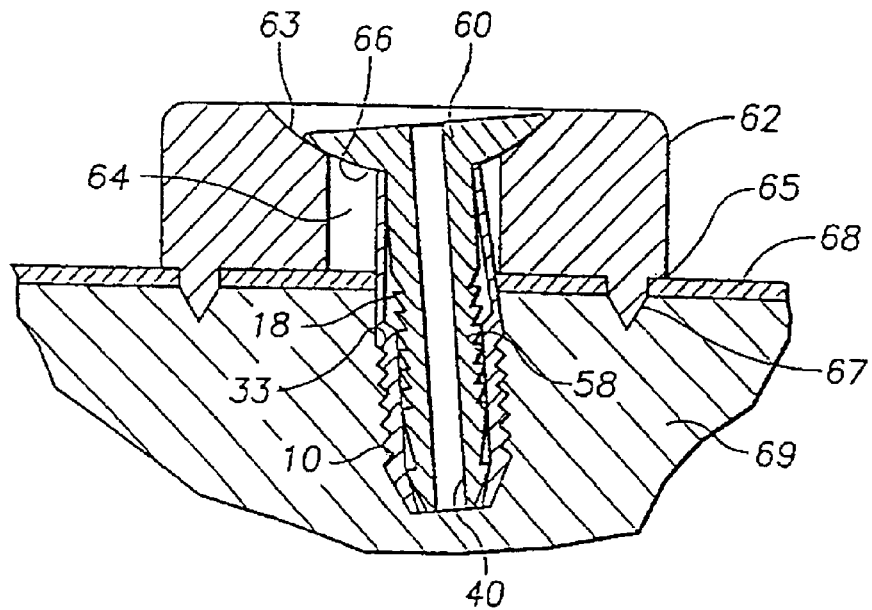
FIG. 11 is a cross-section illustrating an insertion element rivet and washer of FIG. 6 in place within expandable element in a bone opening.

FIG. 11 illustrates an insertion element rivet 58 and washer 62 of FIG. 6. The rivet is in place within expandable element 10 in bone opening 33. FIG. 11 also illustrates how projections 67 are inserted into tissue 68 and bone 69 to provide a grasping surface for the washer 62. All other reference numbers are as previously disclosed. FIG. 11 particularly illustrates the floating nature of rivet 58 within its captured washer 62, allowing insertion in the bone at angles other than exactly orthogonal to the tissue and/or bone surface.

In further embodiments, one or both of the washer surfaces 63, 65 may include a means for enhancing tissue proliferation on the washer after it is inserted into the tissue and bone opening. This means for enhancing tissue proliferation can include a plurality of small apertures (not shown in FIG. 6) defined between the upper and lower surfaces 63, 65 of the washer 62, these apertures disposed on a peripheral portion of the upper and lower surfaces. Further, tissue proliferation can be enhanced by including one or more roughened portions (not illustrated) on either, or both, of the upper and lower surfaces of the washer. The washer and/or insertion member could also be coated or impregnated with a variety of bone and tissue growth enhancing factors such as, for example, hydroxyapatite, calcium phosphate, and the like. Preferably, the washer is made of a bioabsorbable material identical to those described above. The chemical composition of the washer may be chosen so that it will be absorbed completely once the tissue fixed by the rivet has reattached itself to the bone. Moreover, the insertion element may also comprise a bioabsorbable material, as described above with regard to the expandable element.

A significant advantage of the rivet configurations of the present invention is that the operator can set the compressive force between tissue, fastener, and bone by manually adjusting the pressure of the rivet against the tissue at the time the tissue is being fastened.

FIG. 7 illustrates in a less diagrammatic cross-sectional view, a suture fastener 11 of the invention emplaced in a pre-drilled hole 33 in bone. FIG. 7 shows deformation of the outer portion of expandable member 10 within irregularities in the bone hole wall. This deformation results from the forcible expansion of the expandable member within the bone hole and has two major effects: (i) the density of the bone surrounding the expandable member is increased by the forces exerted upon the bone and (ii) a bulge is created underneath the outer bone surface causing interference between the insertion element and the exit diameter of the bone hole.

The insertion element 34 has been compressed into the axial channel 18 of an expandable member 10, the proximal projection 38 of the insertion element 34 expanding the member's outer surfaces 13 thereof against the wall 30 of the bone hole 33. The term "compressed" refers to a force lacking impact or impulse. The suture 46, which can be, for example, a standard braided dacron suture, is knotted against the proximal end 36 of insertion element 34, passes through axial channel 40 and out of the fastener 11 where it can be used to attach soft tissue to the bone at the fixation site. The severed axial releasing structure 15 is also illustrated at distal end 14 of expandable member 10.

FIG. 8 illustrates an embodiment in which proximal projection 38 is placed so that it extends out of the proximal end 12 of expandable member 10. In this configuration, a shoulder 168 of proximal projection 38 engages flat portion 21 at the proximal end 12 of the expandable member 10. All reference numbers are identical to those presented above. This engagement provides added security to the bone fastener to prevent the insertion element from backing out of the expandable member.

FIG. 9 illustrates a further embodiment in which a step 20 is defined in the inner surface 19 of axial channel 18. The step is adapted to mate with a corresponding ridge 39 on the outer surface of insertion element 34'. Alternate embodiments may include a plurality of steps and ridges as well. All reference numbers are identical to those presented previously.

The insertion element mates with the axial channel of the expandable member. Accordingly, its size may also vary over wide limits. Exemplary insertion elements designed to mate with the expandable members described previously are about 0.44 inches (11.1 mm) long with a channel diameter of about 0.060 inches (1.5 mm). The rivet type insertion element (see FIG. 6) has a distal radial projection about 0.180 inches (4.6 mm) wide, with a total length of about 0.5 inch (12.7 mm). An exemplary slidable suture element (see FIG. 5) is about 0.47 inches (11.9 mm) long, with a distal bore about 0.05 inches (1.3 mm) across and 0.04 inches (1.0 mm) deep. An exemplary washer designed to mate with the rivet of FIG. 6, is about 0.29 inches wide, with a central bore about 0.14 inch (3.5 mm)". A total of six projections may be equally spaced around the lower washer surface, each projection about 0.065 inches (1.6 mm) long.

C. Holding Means

Figure 12:
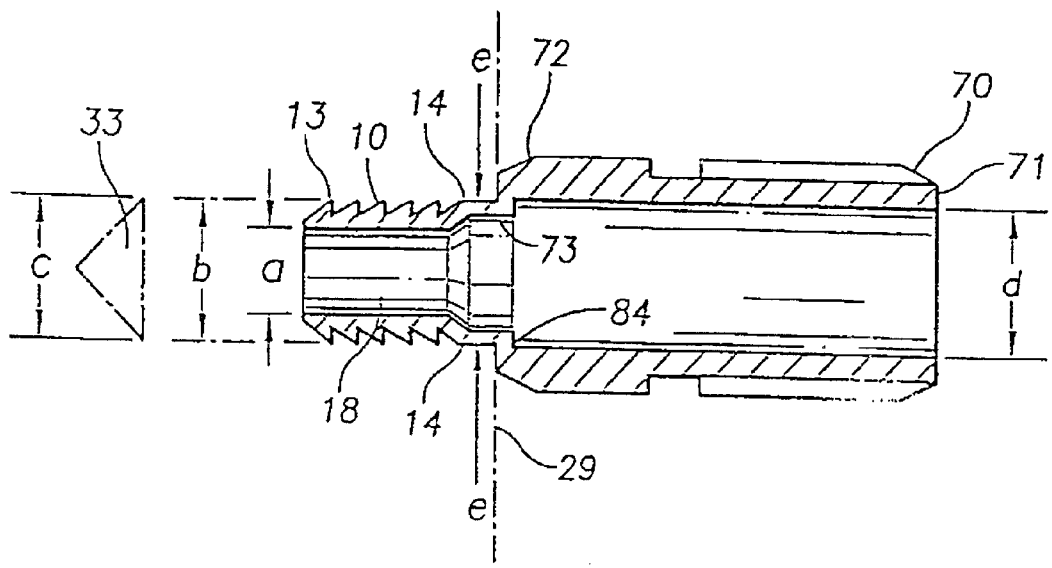
FIG. 12 is a diagram showing emplacement of expandable member within bone hole using a preferred holding means.

FIG. 12 shows emplacement of member 10 within bone hole 33 using a preferred holding means 70 which is adapted to provide for firm deployment of the fastener without imposing substantial forces upon the bone itself in directions toward or away from the bone. In FIG. 12, expandable member 10 having axial channel 18 and outer surface 13 is shown in an unexpended state at which the axial channel 18 has a diameter (a) and the outer surface 13 has a diameter (b) at its widest point or points. Diameter (b) may be equal to the diameter (c) of the bone hole so that expandable member in an unexpended state passes into a hole in a light, press-fit configuration. The holding means 70 is an elongated, substantially hollow tube 71 having an inside diameter (d) greater than the outside diameter (e) of distal end 14 of expandable member 10.

The proximal end 72 of holding means 70 is integral with the distal end 14 of the expandable member 10. The term "integral" refers to a variety of configurations in which the proximal end of the holding means is in physical communication with the distal end of the expandable member. The term "integral" refers to units made of one piece of material as well as components which may be separate initially but are later joined to form a complete device. In the embodiment of FIG. 12, this physical linkage may be via a continuous, unbroken surface 73 extending between the holding means 70 and expandable member 10.

Nevertheless, a single, continuous surface is not necessary between holding means 70 and member 10. Expandable member 10 may be snap-or press-fit into position at the proximal end of holding means 70 using a variety of mechanisms. Referring to FIG. 13, the proximal end of expandable member 10 is press-fit into a bore 71 defined at proximal end 72 of holding means 70. The expandable member 10 may include one or more detents 74 adapted to engage with corresponding surfaces 76 on the holding means 70.

FIG. 14 illustrates a two-piece holding means 70 having an intermediate end 72 supplied with a series of screw threads 75. A corresponding series of screw threads 78, designed to mate with threads 75, are disposed at a second, intermediate end 73.

Figure 25:
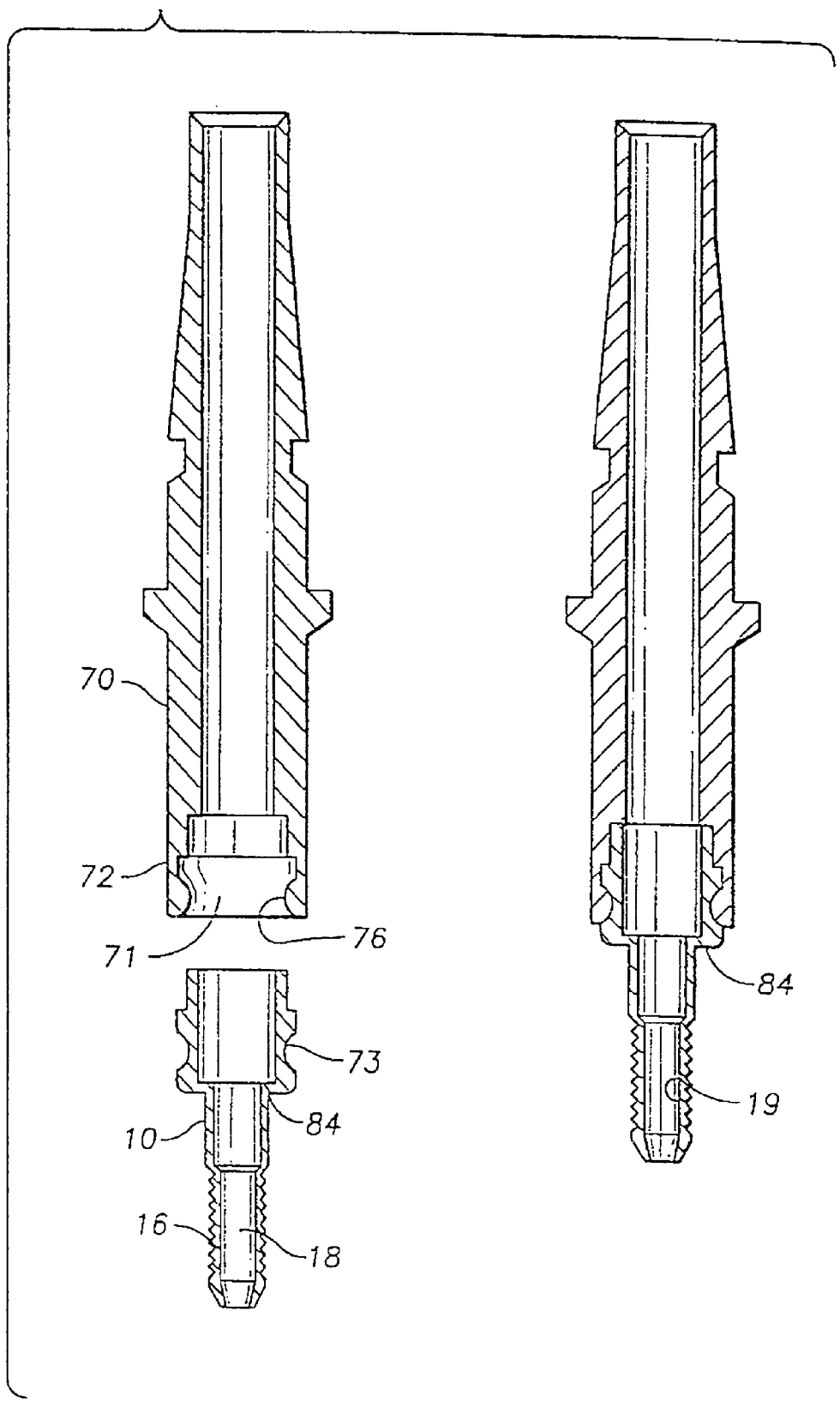
FIG. 25 is a cross-section of another embodiment of an expandable member and holding means of the invention.

FIG. 25 illustrates another way of integrating the proximal end of holding means 70 with expandable member 10. As illustrated, proximal end 72 of holding means 70 is provided with a bore 71 having surfaces 76 designed to mate with corresponding detents 74 on expandable member 10 in a manner allowing expandable member 10 to be spun onto holding means 70 or crimped onto holding means 70. All other reference numbers are as described previously. Thus, in FIGS. 12–14 and 25, the expandable member 10 is constructed to allow the holding means 70 to maintain engagement with the expandable member during the steps of emplacement in the bone.

Moreover, each of the embodiments of FIGS. 12–14 and 25 includes a structure for axially releasing the expandable member from the holding means. The manner of activating the axial releasing structure is described below but it will be appreciated that the structure may be arranged as a substantially annular ring or membrane of material. In FIGS. 12–14 and 25, axial releasing structure is a frangible membrane 84. The term "frangible" refers to a membrane that is breakable or fragile. In particular, FIG. 12 illustrates frangible membrane 84 as an annular attachment portion connecting holding means 70 and expandable member 10. FIG. 13 illustrates frangible membrane 84 connected the distal end of expandable member 10 to a detent 74, the membrane between detent 74 and member 10 severable during emplacement of the fastener, as described below. FIG. 14 illustrates frangible membrane 84 disposed between distal end 14 of the expandable member 10 and a threaded portion 75 of holding means 70.

Figure 15:
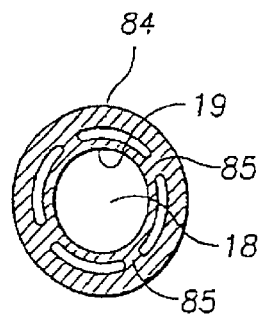
FIG. 15 is a cross-section of a frangible membrane of the invention.
Figure 16:
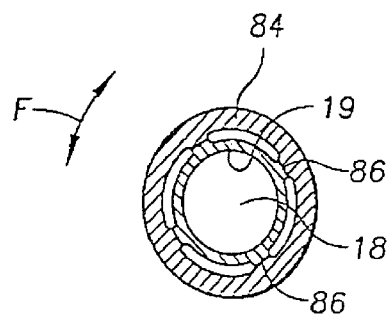
FIG. 16 is a cross-section of another embodiment of a frangible membrane of the invention.

The axial releasing structure, however, may be other than a complete annulus of frangible material. In FIG. 15, the membrane 84 is a series of spokes or webbing 85. In this configuration, only the spokes need be broken. Alternately, as shown in FIG. 16, the structure for axially releasing the expandable member is a plurality of very attenuated membranes 86.

An exemplary holding means may have a diameter of between about 0.070–0.140 inches (1.7–3.5 mm) and is integral with the expandable member (see FIG. 12) by way of an annular frangible membrane about 0.01–0.02 inches (0.25–0.50 mm) thick.

D. Methods

One method, although by no means the only method, for attaching soft tissue to bone will be described below with reference to the rivet fastener of the present invention.

To attached soft tissue to bone, a surgeon takes the sharpened proximal end of a K-wire (manufactured, for example, by Kirschner Medical Company) and spears the tissue that is to be attached. The proximal end of the K-wire is then placed over the bone surface at the approximate site of attachment. The K-wire is then drilled into the bone at that site. If the location is where the surgeon wants it, the surgeon then threads a cannulated drill of the appropriate size over the K-wire. A hole is then drilled into the bone using the cannulated drill. Then drill is then removed, leaving the K-wire in place. The rivet of the invention is then loaded into an expandable member contained within an emplacement apparatus (described below with reference to FIGS. 23 and 24). The rivet is run over the K-wire and the expandable member pressed downwards through the tissue and into the bone hole so that the expandable member is emplaced into the bone hole. If the surgeon decides that the orientation of the bone fastener and soft tissue is correct, the emplacement apparatus is triggered to set the bone fastener within the bone hole. The emplacement apparatus and then the K-wire are removed in turn. Other variations on this technique include first drilling a bone hole and then punching a hole through the soft tissue. The tissue is then moved over the bone hole using, for example, a K-wire or a grasping device. The K-wire is inserted into the hole in the soft tissue and bone and then the emplacement apparatus of the invention is threaded over the K-wire.

The preferred method includes providing an expandable member for insertion into an opening in the bone, the member having defined in it an axial channel with a certain diameter, as described above. The expandable member includes a structure for axially releasing it from a holding means. The expandable member is grasped at the distal end using the elongated holding means described previously. The expandable member is inserted into a bone opening with the holding means while maintaining contact with the distal end of the expandable member. A compressive force, which may be continuous, is applied to the expandable member in order to expand the diameter of the axial channel so that an outer surface of the expandable member engages the bone. The force is applied by compressing the elongated insertion element into the axial channel of the expandable member. The projecting portion at an outer surface of the insertion element is engaged with the inner surface of the axial channel of the expandable member to exert a force substantially orthogonal to the axial channel. The diameter of the axial channel expands within the bone opening as the projecting portion travels proximately within the axial channel. The means for axially severing the expandable member is then activated, so that the expandable member, fully expanded into the bone opening by the inserted element, is released from the holding means when the continuous, compressive force stops. In particular, when the frangible membrane is axially severed, the expandable member is disengaged from its holding means.

It is an important feature of the present invention that the force needed to expand the expandable member may be substantially continuous and spread out over time so that the force is not an impulse, as in prior art methods. The expandable member is expanded using the insertible element with a compressive motion that is axially delivered in a direction substantially parallel to the longitudinal axis of the insertion element. Thus, the apparatus for inserting a bone fastener requires an advancing drive mechanism which lacks any impact or impulse characteristics. In physical terms, it can be considered that the system of: (i) a bone; (ii) a K-wire to guide a drill to make an opening in the bone; (iii) a bone fastener emplaced over the K-wire in the opening; and (iv) an apparatus for emplacing the bone fastener, comprises a closed, continuous boundary system in which no external forces are applied to the system such as, for example, by a hammer or impactor.

Figure 17:
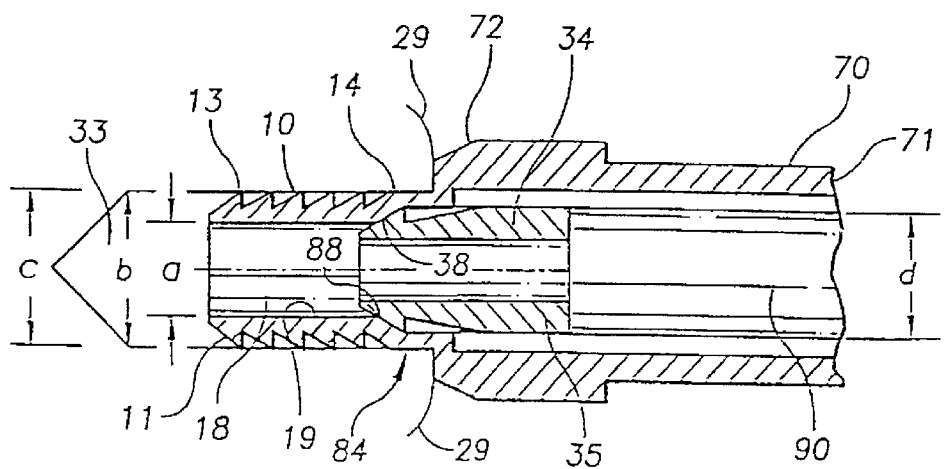
FIG. 17 is a cross-section showing emplacement of a bone fastener within a bone hole using an apparatus of the present invention.

FIG. 17 shows emplacement of a bone fastener 11 within a bone hole 33 using an apparatus of the present invention. The bone surface is indicated as reference number 29. Insertion element 34 has at least one projection 38 in facing relationship to a beveled portion 88 along inner surface 19 of axial channel 18. A plunger 90 surrounded by a releasing element 92 (not shown in FIG. 17) is directed from a first position, where the plunger is remote from insertion element 34, to a second position, where the plunger is engaged with the distal end 35 of insertion element 34. The plunger and releasing element 92 are coaxially aligned within hollow tube 71 of holding means 70. The plunger 90 is then further urged forward, pressing insertion element 34 before it into the axial channel 18 of the expandable element 10.

Figure 18:
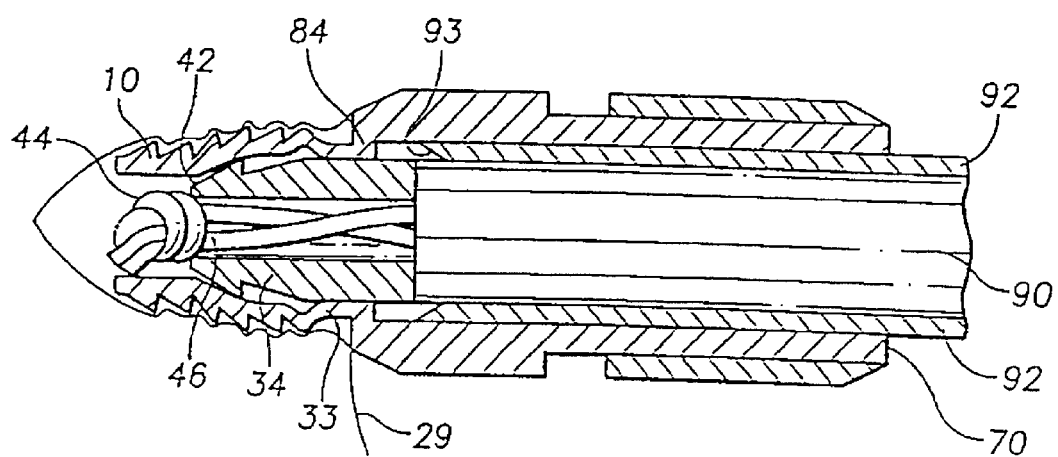
FIG. 18 illustrates one step in the expansion of the expandable member using the method and apparatus of the invention.
Figure 19:
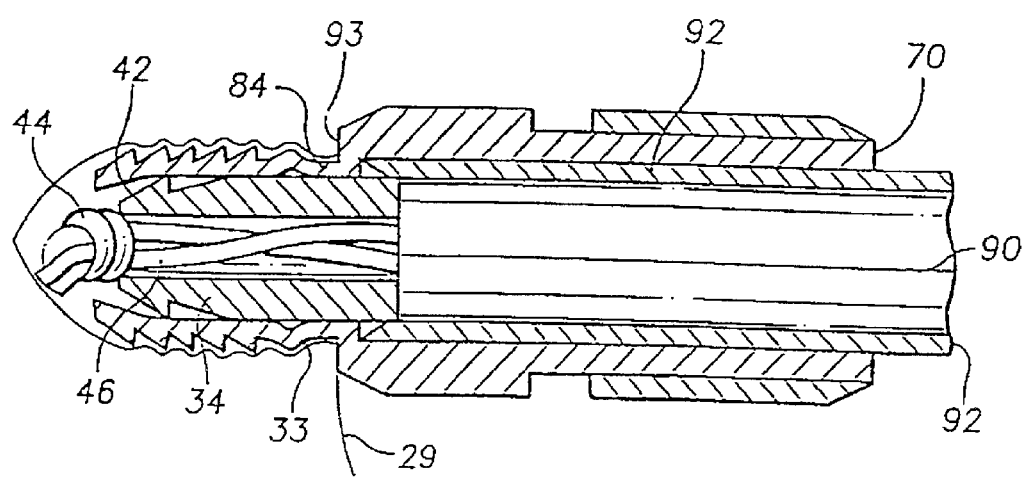
FIG. 19 shows a second step in the progress of expansion of the expandable member.

FIGS. 18 and 19 show the progress of expansion of member 10 as the proximal projection 38 of insertion element 34 presses outward against the inner surface 19 of axial channel 18. In FIGS. 18 and 19, releasing element 92 is shown with a proximal shearing surface 93 which may be a beveled blade. Any proximal surface sufficient to shear the frangible membrane would be sufficient. Also illustrated in FIGS. 18–19 is a suture 46 whose knot 44 is engaged with the suture attachment means 42 at the proximal end of the insertion element 34.

Insertion element 34 is forced frontward to its full extent as shown in FIG. 19. As insertion element 34 approaches its full frontward position, the surface 93 of releasing element 92 approaches, then meets, and then passes through the structure for axially releasing expandable member 10 (e.g., frangible membrane 84), severing the expandable member 10 from the hollow holding means 70, and thereby freeing the fully expanded and firmly fixed fastener 11 from means 70. It will be appreciated that element 92 may have a completely annular distal surface 93 to coincide with the annular structure of the frangible membrane 84 illustrated above. If the frangible membrane 84 includes a series of discontinuities, as illustrated above in FIGS. 15–16, then the releasing element 92 can have shearing surfaces that are also discontinuous.

The holding means 70 is then withdrawn from the site, leaving the fastener in place at the fixation site in the bone.

Figure 20:
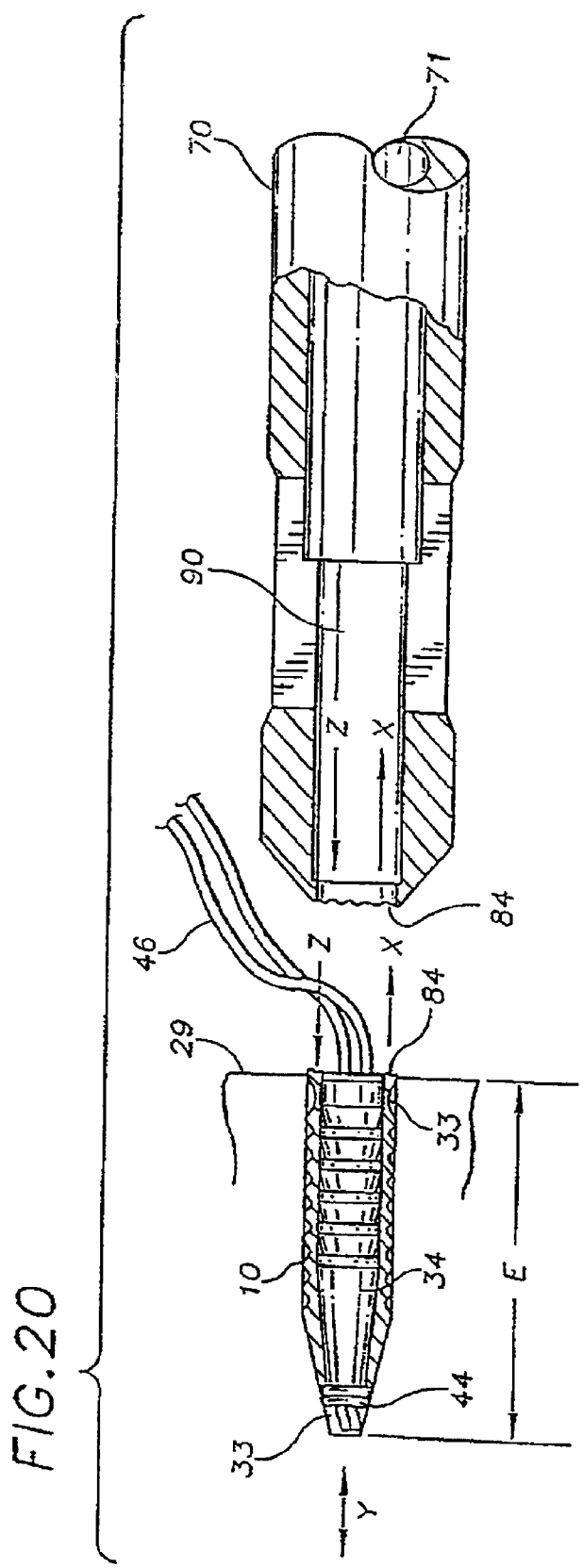
FIG. 20 illustrates an expandable member emplaced in a bone hole and an insertion element in its full frontward position just after axial release from holding means.

Alternately, the frangible membrane 84 may be severed without using a releasing element. One embodiment of the invention relies on the inherent resiliency of the frangible membrane and the failure of the membrane during tension and elongation. Referring now to FIG. 20, an expandable member 10 is shown emplaced in a bone hole and an insertion element 34' in its full frontward position just after axial release from holding means 70. If the bone hole 33 is of a depth (E) that is substantially identical to the length of the expandable member 10, a force (solid arrow X) will be exerted on membrane 84 in a direction substantially parallel to the longitudinal axis of the expandable member (double-headed arrow Y) but in a direction opposite the compressive force (solid arrow Z) exerted by the plunger 90 in its coaxial travel within the hollow tube 71 of holding means 70. It will be appreciated that the magnitude of compressive force Z is substantially equal in magnitude and opposite in direction to force X. Forces X and Z will activate the axial releasing structure (e.g., the frangible membrane 84) by forcing it to elongate and stretch in the same direction. At a certain point, when force X is greater than the strength of frangible membrane 84, the membrane 84 will fail, thus releasing the expandable member and insertion element from the holding means. Suture 46 and knot 44 are also illustrated. This type of releasing mechanism is dependent on the physical properties of the frangible membrane and the rate of shear.

The same forces can be obtained by providing the insertion element as a rivet 58 as illustrated in FIG. 6. In this case, plunger 90 engages the radial projection 23 of the rivet 58 which is stopped against the bone surface. This engagement provides the forces necessary to elongate and stretch the frangible membrane to its breaking point.

With regard to embodiments in which the frangible membrane 84 includes a series of attenuated membranes (see FIGS. 15 and 16), the front-to-rear dimension of each of the membranes is sufficiently thick so that it can withstand the counterforce required to balance the force of urging the insertion element into the axial channel of the expandable member. But the connection of the frangible membrane to the expandable member is thin enough so that, with the insertion element fully inserted and the expandable member affixed in the bone hole, the emplacement means can be rotated about its long axis as indicated by arrow F in FIG. 16, to snap off the connections 86, freeing the expandable member from the holding means.

Figure 21:
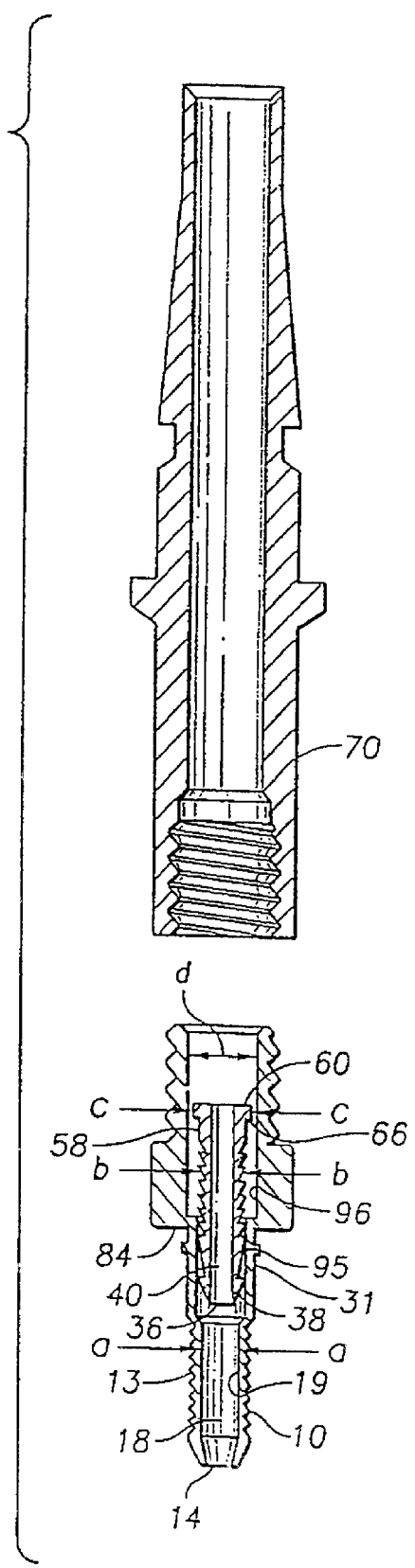
FIG. 21 is a cross-section of one type of holding means adapted for use with an insertion element in the shape of a rivet.

FIG. 21 shows a view of one type of holding means 70 adapted for use with an insertion element 58 in the shape of a rivet. Such an insertion element and holding means are also described above with respect to FIGS. 6 and 14. The element 58 has an axial channel 40. The generally cylindrical holding means 70 has an inside diameter (d) greater than the outside diameter of the distal end 14 of expandable member 10, and great enough to accommodate the diameter of distal projection 38 of insertion element 34', as described above in FIG. 5. The expandable member 10 includes frangible membrane 84. The expandable member 10 passes without resistance into a bone hole as described above generally, and the member is positioned within the hole so that in an externally smooth neck portion 31 projects above the bone surface to provide a stand-off between the radial projection 60 of the insertion element and the bone surface. An annular projection 95 on the neck 31 may retain the washer (not shown) of the rivet insertion element 58, preventing loss of the washer during insertion of the expandable member into the bone hole. The bore of the washer is designed to receive the expandable member prior to emplacement of the bone fastener of the invention.

The outer diameter (b) of the insertion element 58 is about the same as or slightly smaller than the inner diameter of the neck portion 31 of the expandable member. Outer diameter (b) is larger than the inner diameter (a) of the axial channel 18 of the expandable member 10 so that, as the rivet shaft is compressed into the axial channel 18, it passes without resistance through the neck portion 31 but causes the outer, bone engaging surface 13 to expand outwardly against the wall of the bone hole. That is, as the rivet is urged frontward, the radial projection 38 at its proximal end 36 presses outward against the inner surface 19 of the axial channel.

Moreover, the outer diameter (c) of radial projection is sized to interfere with the axial releasing structure (e.g., frangible membrane 84). When this occurs, the progress of the rivet within the expandable member 10 is momentarily stopped. Further frontward compression of the rivet 58 drives its radial projection 60 through the frangible membrane 84 and causes a failure of the frangible membrane portion, effecting separation of the fully installed rivet from the holding means 70. Then, the holding means 70 can be withdrawn from the site. Preferably, lower surface 66 of radial projection 60 is provided with an abrupt proximal edge to effect a shearing action. A circular undercut 96 on the frangible membrane further improves the precision of the separation. Thus, the resulting rivet is anchored firmly in place within the bone hole by intimate contact of the outer surface of the expandable member with the bone hole. Further, the material to be fastened by the rivet is confined about the supported neck portion of the expandable member between the bone surface and the washer of the rivet. As described above with regard to FIG. 6, projections 67 on the rivet washer 62 serve to further engage the tissue with the fastener system.

The method of inserting an expandable member 10 in the shape of a rivet (as shown in FIG. 3) is substantially identical to the method described previously for the insertion element rivet. Thus, the proximal end 12 of the expandable member 10 is contoured to pass easily through tissue. The distal, radial projection 23 on the expandable member is attached to holding means 70 by way of a frangible membrane 84, as described above. The membrane may be detached by the methods described previously, thereby freeing the fully expanded and firmly fixed rivet fastener from the holding means. The holding means is then withdrawn, leaving the expandable member rivet in place at the fixation site of the bone, compressing the attached tissue between the prominal end of the radial projection and the surface of the bone. An alternate configuration for use in the rivet described immediately above, includes an annular undercut 98 on an inner surface of the radial projection 23, this excavation being just proximal to the frangible membrane 84. The undercut is formed sufficiently deeply into the material of the radial projection 23 so that when the frangible membrane is cut or otherwise severed, an annular fragment is cut free of both the radial projection 23 and the expandable member (not shown), and any remaining connection between the radial projection and the expandable member being so thin has to provide little resistance to simply pulling the holding means away from the fixed fastener. All other reference numbers are as previously described.

E. Apparatus

A preferred emplacement apparatus of the invention retains the holding means and expandable member prior to emplacement. The emplacement apparatus includes means for pressing the insertion element into the expandable member and then separating the expandable member from the emplacement apparatus. The fastener assembly can include a disposable cartridge, the cartridge containing the expandable member, insertion element, holding means, and means for attaching the disposable cartridge to the apparatus.

Figures 22, 23:
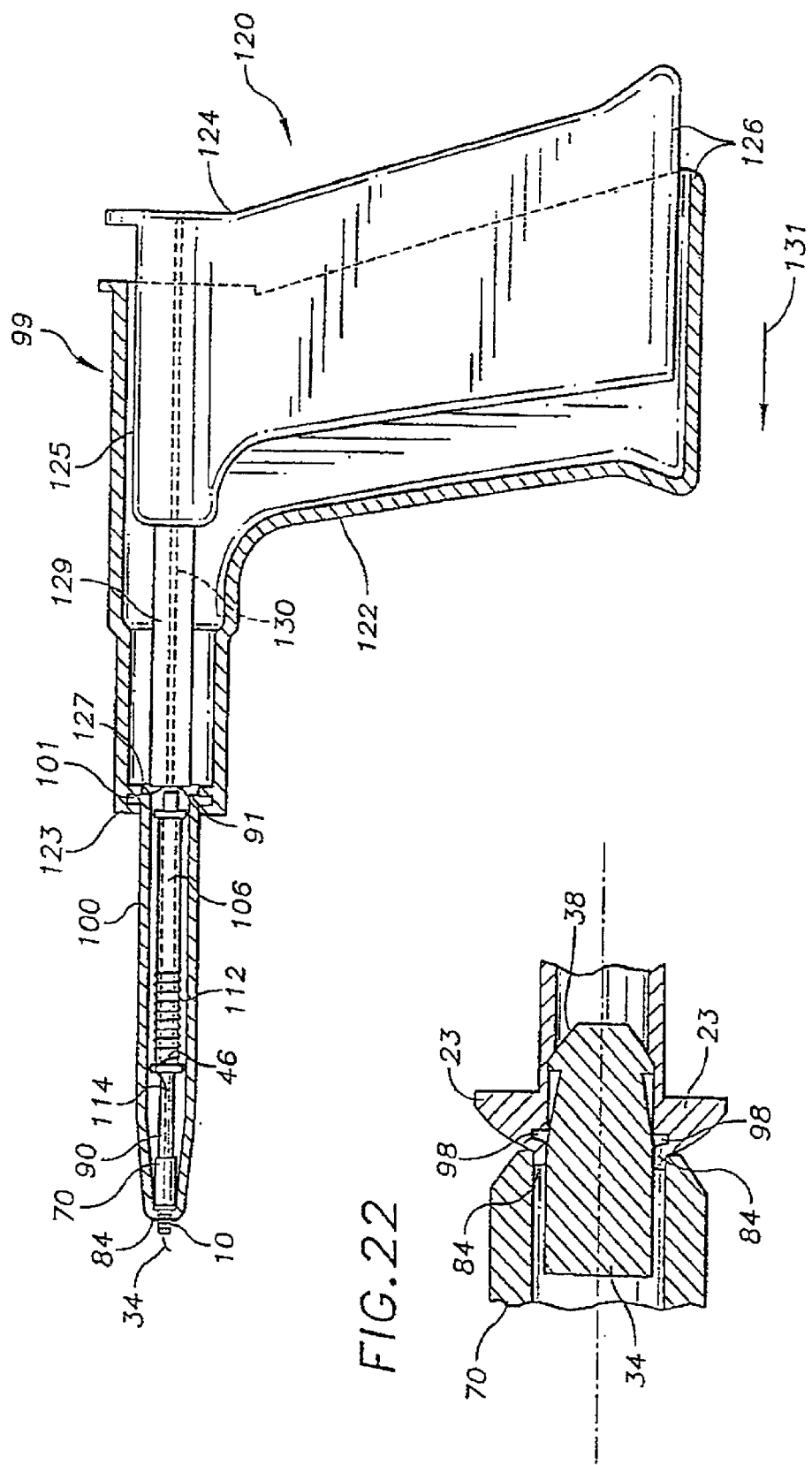
FIG. 22 is a cross-section of another embodiment of the rivet of FIG. 21.
FIG. 23 is an exploded view of one embodiment of an emplacement apparatus of the invention.

FIG. 23 is one embodiment of an emplacement apparatus of the invention. Its operation is best exemplified by reference also to FIGS. 18 and 19. The apparatus 99 includes a cartridge 100 which encloses holding means 70 attached by axially releasing membrane 84 to expandable member 10. The cartridge is preloaded with plunger 90 and insertion element 34. A releasing element 92 (not shown in FIG. 23) is co-axially arranged around plunger 90 to activate the axial releasing structure (e.g., sever the membrane 84). The insertion element 34 is positioned with its proximal projection 36 in facing relationship to distal end 14 of the expandable member 10. Insertion element 34 is provided with a suture 46. The free ends of the suture pass through the axial channel 40, through channel 106 of the plunger 90, and are knotted against the proximal end 36 of the insertion element 34. The knot 44 is fully contained within the expandable member 10 prior to its emplacement in the bone hole, so that it cannot interfere with the insertion into the hole.

The cartridge 100 may additionally include a take-up spool 112, for storage of the free ends of suture 46. When the apparatus is loaded, suture 46 is arranged to pass from the knot in proximal end 36 of insertion element 34, through axial channel 40, through a hole in plunger axial channel 106, and over and around spool 112. As the apparatus is withdrawn, leaving the fastener with the suture 46 attached fixed in place in the bone hole, as described above with reference to FIGS. 18–19, the free ends of the suture 46 pay off from the take-up spool 112.

Cartridge 100 is removably attached to hand-held means for urging the plunger 90 frontward (i.e., towards the bone) with respect to the cartridge. In the configuration of FIG. 23, the hand-held means 120 consists of two handle elements 122, 124 slidably engaged to provide a comfortable pistol grip 126 by which handle element 124 can be moved in a front-and-rear direction with respect to the handle element 122 by squeezing the pistol grip 126. The end 123 of the handle element 122 is adapted for removably mounting the distal end 101 of cartridge 100. The end 125 of handle element 124 includes a push rod 129 whose proximal end 127 abuts the distal end 91 of plunger 90 when the handle elements are assembled and the cartridge 100 is mounted onto end 123 of handle element 122. Alternatively, an axial bore 130 can be arranged to pass rearward through push rod 129 and handle element 124 for conducting the suture distally from the knot at the proximal end of the expandable element all the way to the outside.

With the apparatus so assembled, the surgeon grasps the apparatus by the pistol grip, and directs the expandable member to the desired depth into the predrilled hole in the bone. Then, while holding the apparatus in place, the surgeon squeezes the grip 126 sliding the handle 124 frontward with respect to the handle element 122, as indicated by the arrow 131. The push rod 129 presses against distal end 91 of plunger 90, urging the plunger in a non-impulse fashion towards the holding means 70, and thereby: (i) compressing element 34 into the axial channel 18 of expandable member 10; (ii) causing the expandable member 10 to expand within the bone hole 33; and (iii) causing releasing element 92 to sever the frangible membrane 84 between the expandable member 10 and the holding means 70, leaving the fastener fixed in the bone.

Figure 24:
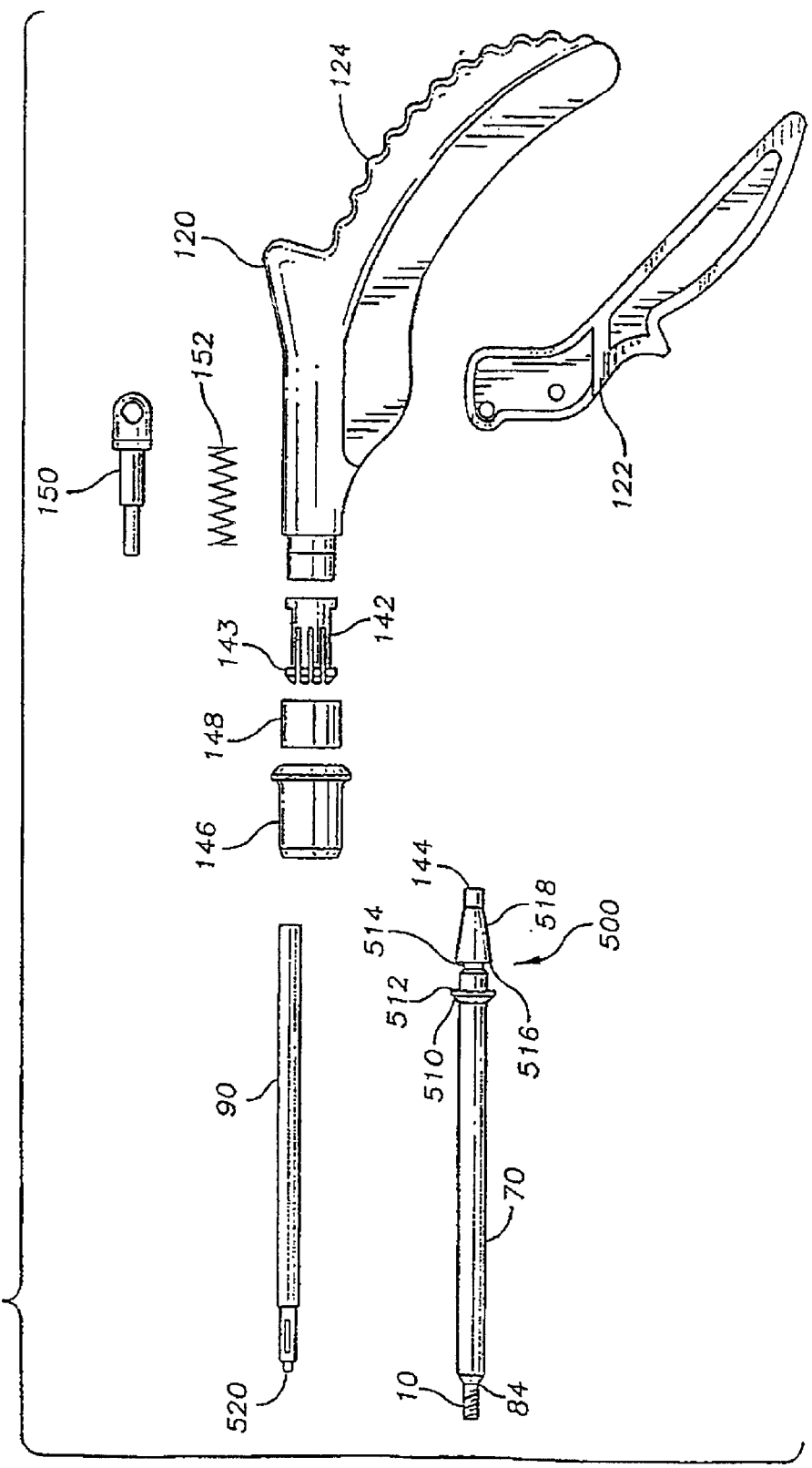
FIG. 24 is an exploded view of another embodiment of an emplacement apparatus of the invention.

An alternate embodiment is shown in the exploded view of FIG. 24. All reference numbers are identical to those in FIG. 23, unless noted otherwise. The holding means 70 is connected at its distal end by a quick-connecting interlock 500 with the hand-held means 120 for urging a plunger 90 frontward with respect to the expandable member 10. The apparatus includes a lock mechanism 142 having a series of slots or teeth 143 for gripping the distal end 144 of holding means 70. A cap 146 and cap insert 148 are also provided to co-axially engage the lock 143. An actuator drive rod 150 is positioned within the hand held means and is co-axially arranged with spring 152. The drive rod, connected to handle 122, is forced against plunger 90, as described above.

Preferably the snap-on interlock is configured as an insertible, spring-loaded connector, in which a distal portion of the holding means forms the "male" part of the connector and a portion of the hand-held means forms the "female" part. With reference to FIG. 24, a flange 510 is situated with a rear surface 512 situated a fixed distance distal to the frangible membrane 84 connecting the expandable member 10 to the holding means 70. Distal to the flange 510, is a groove 514 having a frontward-facing surface 516 generally perpendicular to the longitudinal axis of the holding means. The holding means tapers distally from the outer edge of the surface 516. The hand held means is provided with a generally cylindrical bore for receiving that portion of the holding means situated distal to the flange.

The hand-held means 120 is provided with one or more keepers (not shown) that are moved away from its longitudinal axis by the advancing taper 518. The keepers then spring into the groove 514 and lock against frontward-facing groove surface 516 when the distal portion of the holding means is correctly positioned within the receiving bore of the hand-held means. The rear-facing surface 512 of the flange 510 contacts a part of the hand-held means adjacent the holding means receiving bore to provide a stop establishing the correct rearward position of the holding means within the hand-held means.

The hand-held means 120 is provided with a plunger 90 that can be continuously urged proximally with respect to the holding means receiving bore along the holding means longitudinal axis. Continuously and without impulse, the insertion element is driven toward, and into, the axial channel of the expandable member. The plunger 90 includes a shoulder 520 at its proximal end. An edge of the shoulder provides a sharpened surface sufficient to activate the releasing structure by severing frangible membrane 84.

Preferably, the length of the plunger is fixed in relation to the fixed front-to-rear distance between the rear surface 512 and the frangible membrane connecting the expandable member to the holding means. A stop is provided to limit the extent frontward to which the plunger can be urged within the hand-held means, so that the disengagement of the expandable member from the holding means is complete at just the point where the plunger has been moved to its proximal limit. This ensures proper emplacement of the fastener in the bone hole, provided that the holding means is properly mounted in the handle and the user urges the plunger frontward as far as it will go.

The components of the bone fastener of the invention may be included in a surgical fastener kit. An exemplary kit may include an expandable member of the invention; an insertion element of the invention and a holder for engaging with the expandable member, the holder capable of maintaining the expandable member in position with the bone opening. Other embodiments of the kit may include a grasper/manipulator for grasping free ends of the suture to pass the suture through soft tissue. Such a suture-grasping device is described in commonly assigned and co-pending application Ser. No. 09/097,154, filed Jul. 26, 1993, incorporated herein by reference. A K-wire, drill and drill guide may also be also included. Preferably, the kit is encased in a sterile tray or other receptacle for use by an operator at a site.

The invention will be further illustrated by the following Example.

EXAMPLE

An expandable member is formed of natural high density polyethylene ("PE"), type PDC 9122, supplied by Dow Chemical Co. (Dow HD8354N) and dimensioned to slide easily into a 0.138 inch (3.5 mm) diameter bone hole. The outer surface of the member is molded to a 6-32 screw thread configuration to provide screw threads. A 6-32 screwthread configuration provides a 0.138 inch outermost diameter so that the member can be inserted into a 3.5 mm bone hole without resistance. The axial channel of the member is of a uniform 0.070 inch (1.8 mm) diameter, and its length is 0.422 inches (10.3 mm).

The insertible element is formed of DuPont Delrin II 500, molded to have the general shape shown in FIG. 4 and an outermost diameter of 0.107 inch (2.7 mm). Delrin is much less deformable than the polyethylene of which the expandable member is made. The proximal leading edge of the insertion element permits the relatively incompressible element to be forced into the 0.070 inch expandable member axial channel and to expand the relatively soft expandable member. When the insertion element has been fully inserted within the expandable member, the device has an outermost diameter approximately 0.160 inch (4.1 mm), providing for substantial deformation of the outer surfaces of the expandable member into the irregular wall of the bone hole, and thereby forming a firm fastener for the expandable member and insertion element. The element has an axial channel of diameter 0.046 inches (1.1 mm), which accepts a pair of sutures for later use in attaching soft tissue to the bone surface. Before insertion of the element, the sutures are passed through the axial channel of the insertion element and their proximal ends are knotted so that they stop against the proximal end of the insertion element.

The outside configuration of the member is a 6-32 thread which provides a series of ridges which assist in permitting deformation of the expandable member in the bone hole and conformation of the expandable member outer surface as it is pressed into the 0.138 inch (3.5 mm) diameter bone hole. In this prototype, the threads are not used for turning the expandable member into the bore, but rather to facilitate deformation of the outer portion of the member when the member is expanded within the bone hole. When the insertion element is inserted into the axial channel of the expandable member, the threads are deformed by irregularities in the cancellous bone hole wall, locking the fastener, and the element compressed within it, into place.

The expandable member is formed with frangible, integral connection to a cylindrical holding means as described above, enclosed within a cartridge, and provided with the apparatus as described above, configured and dimensioned as follows:

The holding means, for example as shown in FIG. 24, is formed as a cylinder having inside diameter of 0.145 inches (3.7 mm), outside diameter 0.230 inches (5.8 mm), and a total length of 6.0 inches (152 mm). The frangible membrane between the holding means and the expandable member is formed as an annulus having a thickness of 0.012 inches (0.30 mm).

The plunger and releasing means are constructed by turning a stainless steel rod to provide a punch-and-die configuration (generally as in FIG. 24) having an outer diameter of 0.145 inches (3.7 mm). The severing means is formed by machining the end of the rod to form a sharpened step, located approximately 0.060 inches (1.5 mm) distal to the blunt proximal tip of the plunger.

As the plunger is pressed frontward, it presses the insertion element before it into the axial channel of the expandable member, expanding it and deforming it against the bone hole wall. When the element approaches the point where it has been pressed fully into the member, the sharpened step reaches the 0.012 (0.30 mm) inch thick connecting annulus and passes through it, shearing it and separating the expandable member from the holding means. Then the cartridge is withdrawn together with the plunger and the holding means, leaving the fastener fixed within the predrilled bone hole.

A 3.5 mm (0.138 inch) diameter hole is made in the bone to a depth of about 14 mm using a drill with a stop to limit the hole depth. The prototype device is emplaced as described above, in femur bone recovered from a pig cadaver, and then is tested as follows.

The hole is drilled into the pig femur approximately normal to the bone surface to a depth about 14.25 mm using a step drill. Then a fastener is loaded with a pair of #2 non-sterile braided polyester sutures coupled to a hand-held means, positioned, and fixed in the bone hole as described above. A knot is tied in the sutures at some distance from the fastener and looped over an Ametek Accuforce Cadet digital force gauge, 0–50 lbs. range (Mansfield & Green). The slack in the sutures is taken up by drawing the force gauge by hand away from the fastener in a direction perpendicular to the bone surface. The holding force is then tested by sharply pulling the force gauge away from the bone by hand in a direction perpendicular to the bone surface. In such preliminary tests, the fastener held and the suture broke. These results demonstrate a holding capacity equivalent to those shown in similar tests using known devices now on the market.

The fastener according to the invention provides a platform to secure the suture because it is locked into dense bone, and because the conformity of the expandable member surface with irregularities in the bone provides efficient fixation. Moreover, there are no sharp edges in the fastener that can abrade the suture.

The bone fastener according to the invention can be used for fastening bone to any of a variety of objects, including tissues such as ligaments or tendons and prostheses such as bone plates. The fastener and emplacement apparatus can be used in any of a wide variety of orthopedic surgical procedures and settings. The fastener can provide superior holding capacity and relatively small size, and can be installed according to the invention without impulse, impact or hammering and without imposing any substantial net force toward or away from the bone surface, and so the invention provides for fastening in surgical settings in which bone anchors have not been used, or have been used with limited success.

The fastener according to the invention is of a readily drillable material, and the installed fastener is situated near the bone surface. Thus, removal of the device from the bone in a later surgical procedure is straightforward. If removal of a fastener is indicated, the surgeon can simply use a retrieval device, consisting of for example, a drill bit, preferably of a somewhat smaller diameter than the original bone hole. The drill bit can be used to excavate the insertion element and then the anchor and any debris can be simply withdrawn from the hole.

EQUIVALENTS

It should be understood that various changes and modifications of the preferred embodiments may be made within the scope of the invention. Thus it is intended that all matter contained in the above description be interpreted in an illustrative and not limited sense.

What is claimed is:

1. A rivet for coupling an object to bone for use with an expandable member capable of insertion into an opening in bone, the rivet comprising:

an elongated element for insertion into a distal end of said expandable member, the element having a shaft with proximal and distal ends, the distal end of said elongated element including a radially projecting portion and an outer surface of said shaft including a radially outward projecting portion adapted to expand said expandable member; and a washer having upper and lower surfaces defining a bore therebetween, said bore disposed around a portion of the shaft of the elongated element, and said upper surface of said bore having a radius of curvature that is different than a radius of curvature of a lower surface of said radially projecting portion of the distal end of the elongated element such that, when the upper surface of the bore in the washer and the lower surface of the radially projecting portion on the distal end of the elongated element are in contact, said washer is movable independently of said elongated element.

2. The rivet of claim 1, wherein said washer lower surface includes a plurality of spaced-apart projections extending towards said proximal end of said elongated element.

3. The rivet of claim 1, wherein said washer includes means for enhancing tissue proliferation on said rivet.

4. The rivet of claim 3, wherein said means comprises a plurality of apertures defined between said upper and lower surfaces of said washer at a peripheral portion thereof.

* * * * *